(12) United States Patent
Ozdil et al.

(10) Patent No.: US 7,749,262 B2
(45) Date of Patent: Jul. 6, 2010

(54) INTRALUMINAL STENT DELIVERY SYSTEM, AND METHOD OF TREATING A VASCULAR CONDITION

(75) Inventors: Feridun Ozdil, Santa Rosa, CA (US); Junghwa Jenn Cho, San Francisco, CA (US); Joseph Berglund, Santa Rosa, CA (US); Susan Rea, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 349 days.

(21) Appl. No.: 11/252,450

(22) Filed: Oct. 17, 2005

(65) Prior Publication Data

US 2007/0088427 A1    Apr. 19, 2007

(51) Int. Cl.
*A61F 2/06* (2006.01)

(52) U.S. Cl. .................... 623/1.15; 623/1.28; 623/1.3

(58) Field of Classification Search ................ 623/1.11, 623/1.12, 1.15–1.17, 1.21, 1.22, 1.28, 1.29, 623/1.3

See application file for complete search history.

(56) References Cited

U.S. PATENT DOCUMENTS

| | | | | |
|---|---|---|---|---|
| 5,855,599 | A | * | 1/1999 | Wan .......................... 623/1.22 |
| 2002/0007222 | A1 | | 1/2002 | Desai |
| 2003/0199969 | A1 | | 10/2003 | Steinke |

FOREIGN PATENT DOCUMENTS

| | | |
|---|---|---|
| EP | 0716835 | 6/1996 |
| WO | WO 03/032871 | 4/2003 |
| WO | WO 2004/021923 | 3/2004 |

* cited by examiner

*Primary Examiner*—Anhtuan T Nguyen
*Assistant Examiner*—Jennifer L Hornberger

(57) ABSTRACT

An intraluminal stent, an intraluminal stent delivery system, and a method of treating a vascular condition. The stent includes a framework with a plurality of flap portions projecting substantially beyond a central core region. The flap portions are movable from a compressed position and an extended position when the stent is deployed. The system includes a catheter and the intraluminal stent. The method includes positioning an intraluminal stent within a vessel. A plurality of flap portions of the stent is extended from a compressed position into contact with the vessel.

12 Claims, 9 Drawing Sheets

INTRALUMINAL STENT DELIVERY SYSTEM, AND METHOD OF TREATING A VASCULAR CONDITION

TECHNICAL FIELD OF THE INVENTION

The present invention relates generally to the field of implantable medical devices. More particularly, the invention relates to an intraluminal stent, delivery system, and method of treating a vascular condition.

BACKGROUND OF THE INVENTION

Balloon angioplasty is a medical procedure to widen obstructed blood vessels narrowed by plaque deposits. The procedure may be used in coronary or peripheral arteries. In an angioplasty procedure, a catheter having a special inflatable balloon on its distal end is navigated through the patient's arteries and is advanced through the artery to be treated to position the balloon within the narrowed region (stenosis). The region of the stenosis is expanded by inflating the balloon under pressure to forcibly widen the artery. After the artery has been widened, the balloon is deflated and the catheter is removed from the patient.

A significant difficulty associated with balloon angioplasty is that in a considerable number of cases the artery may again become obstructed in the same region where the balloon angioplasty had been performed. The repeat obstruction may be immediate (abrupt reclosure), which is usually caused by an intimal flap or a segment of plaque or plaque-laden tissue that loosens or breaks free as a result of the damage done to the arterial wall during the balloon angioplasty. Such abrupt reclosure may block the artery requiring emergency surgery which, if not performed immediately, may result in a myocardial infarction and, possibly, death. This risk also necessitates the presence of a surgical team ready to perform such emergency surgery when performing balloon angioplasty procedures. More commonly, a restenosis may occur at a later time, for example, two or more months after the angioplasty, for reasons not fully understood. This reclosure may require repeat balloon angioplasty or bypass surgery. When such longer term restenosis occurs, it usually is more similar to the original stenosis, that is, it is in the form of cell proliferation and renewed plaque deposition in and on the arterial wall.

To reduce the incidence of re-obstruction and restenosis, several strategies have been developed. Implantable devices, such as stents, have been used to reduce the rate of angioplasty related re-obstruction and restenosis by about half. The use of such intraluminal devices has greatly improved the prognosis of these patients. The stent is placed inside the blood vessel after the angioplasty has been performed. A catheter typically is used to deliver the stent to the arterial site to be treated. The stent may further include one or more therapeutic substance(s) impregnated or coated thereon to limit re-obstruction and/or restenosis.

Numerous stent designs are known in the art. A prior art ratchet-locking stent 100 design includes one or more, in this case one, interlocking part joined at a seam 102, as shown in FIGS. 1A and 1B, by one or more locking mechanisms 104 (e.g., locking tabs, ratcheting mechanisms, etc.). The part is formed as a flat sheet and folded upon itself to make up a tubular stent. One consideration in the design of the stent 100 relates to damage to the locking mechanisms 104. In some cases, during assembly, the exposed locking mechanisms may be susceptible to damage during the assembly and crimping (compressing) processes. As such, it would be desirable to provide a ratchet-locking stent with locking mechanisms less prone to damage.

Another consideration in the design of the stent 100 relates to its cross-sectional shape. As shown in a cross-section view in FIG. 1B, the stent 100 has a semi-rounded cross-section due to an apex 106 formed adjacent the seam 102 and/or locking mechanisms 104. Vessels are generally round so it is advantageous to provide a stent that has a complementary cross-sectional shape. This would optimize the delivery of a therapeutic agent to the vessel (i.e., by maximizing surface contact). In some instances, however, vessels are not absolutely round, but are more-or-less "irregularly" shaped. The presence of plaque and/or lesions may contribute to changes in shape. Numerous stent cross-sectional shapes, including rounded and semi-rounded types, may not conform to an "irregularly" shaped vessel. As such, it would be desirable to provide a stent with a cross-sectional shape that is capable of conforming to the vessel.

Another consideration in the design of the stent 100 relates to profile size (i.e., cross-sectional diameter). It is often desirable to provide a small profile size as advancement of a device within the vasculature oftentimes includes navigating many sharp twists, turns, and narrow spaces. Relatively large devices may be more difficult to maneuver through a sometimes tortuous vasculature. Devices with smaller profiles may be less prone to contact the vascular walls during advancement and impart damage to the delicate endothelium. As such, it would be desirable to provide a stent with a relatively small profile size. Furthermore, devices with smaller profiles could better transverse tight lesions where plaque has closed off much of the vessel lumen.

Accordingly, it would be desirable to provide an intraluminal stent, delivery system, and method of treating a vascular condition that would overcome the aforementioned and other limitations.

SUMMARY OF THE INVENTION

A first aspect according to the invention provides an intraluminal stent. The stent includes a framework with a plurality of flap portions projecting substantially beyond a central core region. The flap portions are movable from a compressed position to an extended position when the stent is deployed.

A second aspect according to the invention provides an intraluminal stent delivery system. The system includes a catheter and an intraluminal stent. The stent includes a framework including a plurality of flap portions project substantially beyond a central core region and movable from a compressed position to an extended position when the stent is deployed.

A third aspect according to the invention provides a method of treating a vascular condition. The method includes positioning an intraluminal stent within a vessel. A plurality of flap portions of the stent is extended from a compressed position into contact with the vessel.

The foregoing and other features and advantages of the invention will become further apparent from the following description of the presently preferred embodiments, read in conjunction with the accompanying drawings. The drawings have not been drawn to scale. The detailed description and drawings are merely illustrative of the invention, rather than limiting the scope of the invention being defined by the appended claims and equivalents thereof.

DESCRIPTION OF THE PRESENTLY PREFERRED EMBODIMENTS

Figure 1A:
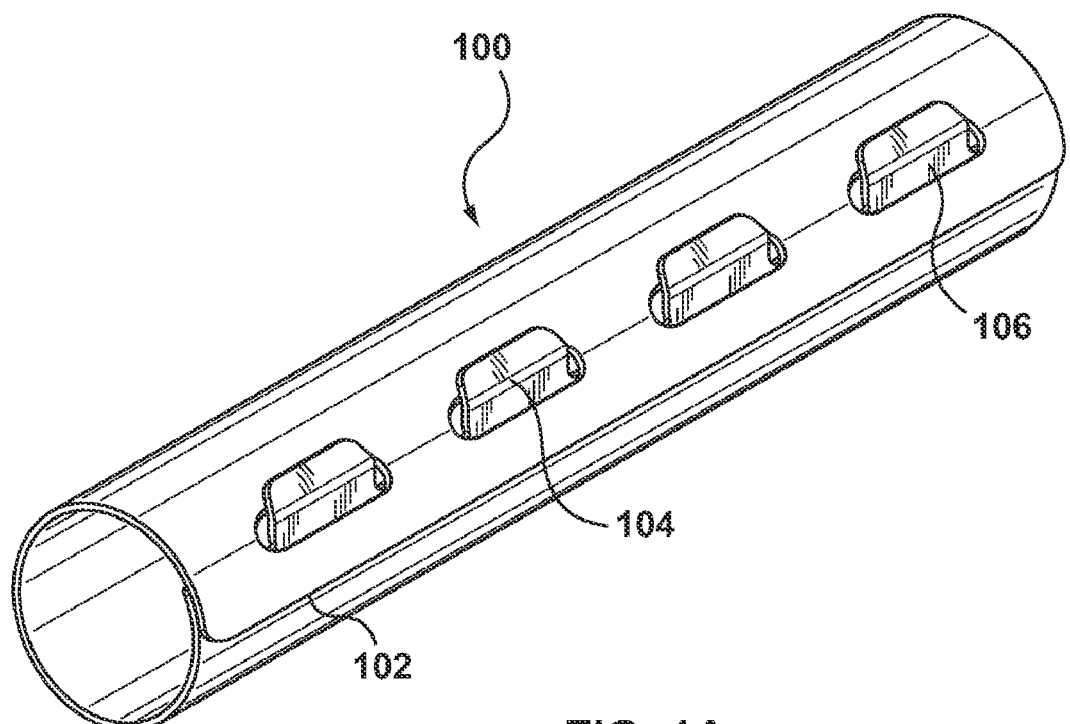
FIG. 1A is a perspective view of a prior art ratchet-locking stent.
Figure 1B:
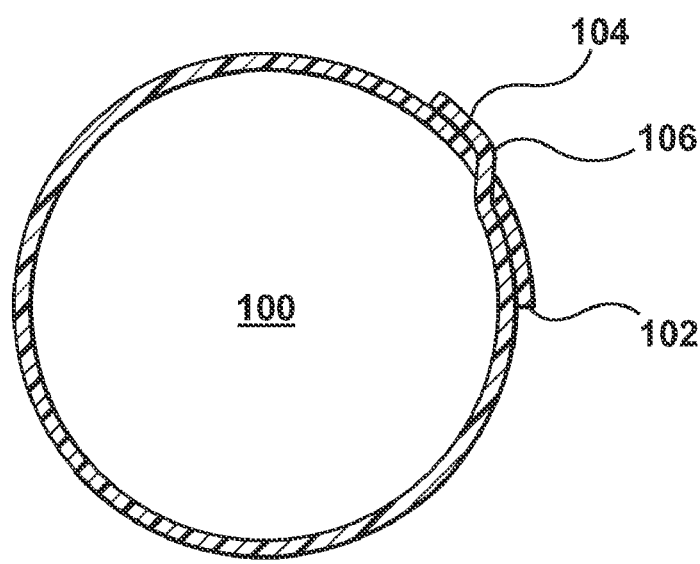
FIG. 1B is a cross-sectional view of the prior art stent shown in FIG. 1.
Figure 2:
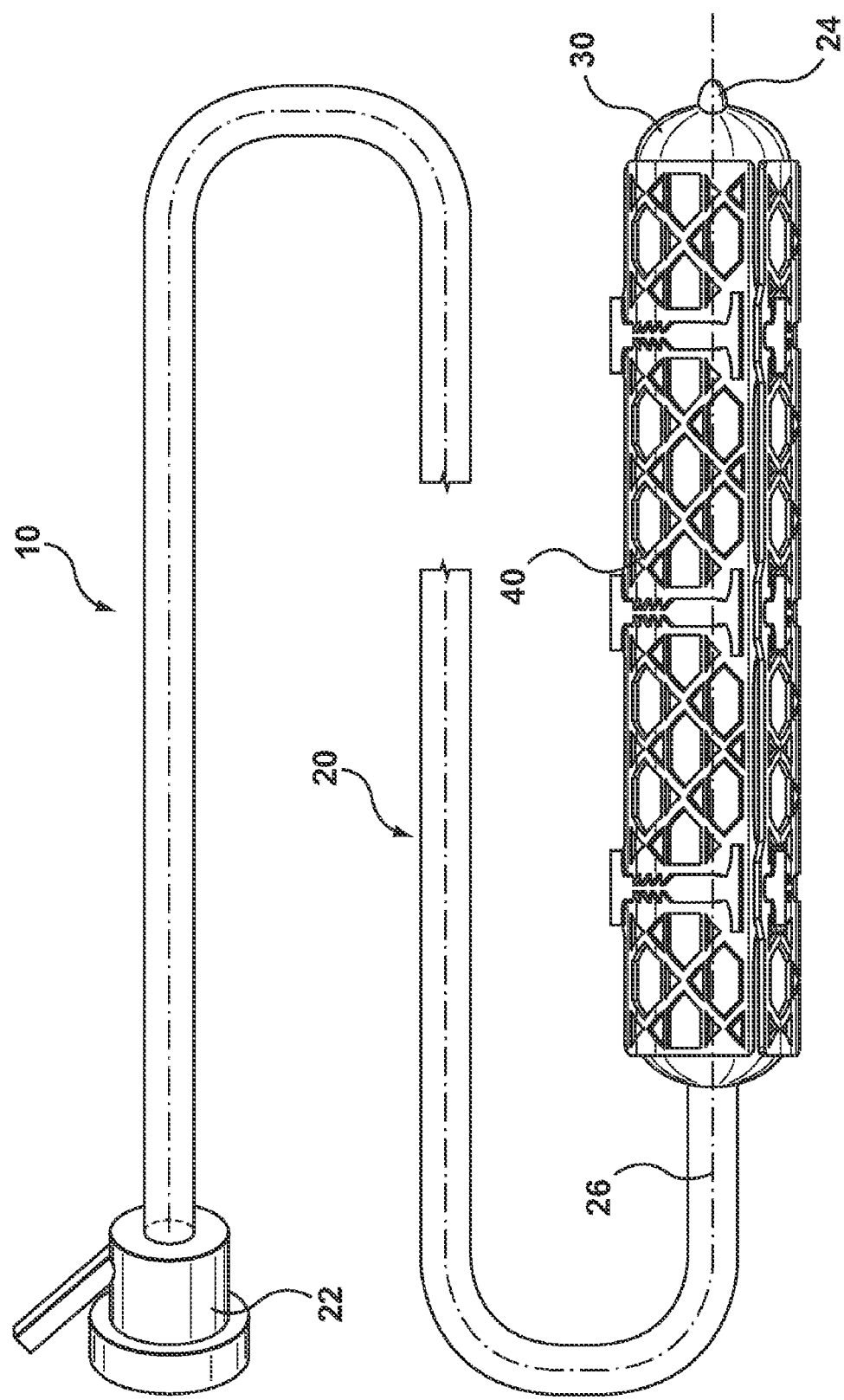
FIG. 2 is a perspective view of an intraluminal stent delivery system, in accordance with one embodiment of the present invention.

Referring to the drawings, which are not necessarily drawn to scale and wherein like reference numerals refer to like elements, FIG. 2 is a perspective view of an intraluminal stent delivery system in accordance with one embodiment of the present invention and shown generally by numeral 10. System 10 may include a catheter 20, a balloon 30 operably attached to the catheter 20, and a stent 40 disposed on the balloon 30. Stent 40 is shown in a compressed configuration and typically remains as such on the balloon 30 during advancement through the vasculature. The compressed stent 40 includes a relatively small profile (i.e., cross-sectional size) to minimize contact with surfaces, such as a vessel wall.

The terms "catheter" and "stent", as used herein, may include any number of intravascular and/or implantable prosthetic devices (e.g., a stent-graft); the examples provided herein are not intended to represent the entire myriad of devices that may be adapted for use with the present invention. Although the devices described herein are primarily done so in the context of deployment within a blood vessel, it should be appreciated that intravascular and/or implantable prosthetic devices in accordance with the present invention may be deployed in other vessels, such as a bile duct, intestinal tract, esophagus, and airway.

Catheter 20 may comprise an elongated tubular member manufactured from one or more polymeric materials, sometimes in combination with metallic reinforcement. In some applications (such as smaller, more tortuous arteries), it is desirable to construct the catheter from very flexible materials to facilitate advancement into intricate access locations. Numerous over-the-wire, rapid-exchange, and other catheter designs are known and may be adapted for use with the present invention. Catheter 20 may be secured at its proximal end to a suitable Luer fitting 22, and may include a distal rounded end 24 to reduce harmful contact with a vessel. Catheter 20 may be manufactured from a material such as a thermoplastic elastomer, urethane, polymer, polypropylene, plastic, ethelene chlorotrifluoroethylene (ECTFE), polytetrafluoroethylene (PTFE), fluorinated ethylene propylene copolymer (FEP), nylon, Pebax® resin, Vestamid® nylon, Tecoflex® resin, Halar® resin, Hyflon® resin, Pellathane® resin, combinations thereof, and the like. Catheter 20 may include an aperture formed at the distal rounded end 24 allowing advancement over a guidewire 26.

Balloon 30 may be any variety of balloons or other devices capable of expanding the stent 40 (e.g., by providing outward radial forces). Balloon 30 may be manufactured from any sufficiently elastic material such as polyethylene, polyethylene terephthalate (PET), nylon, or the like. Those skilled in the art will recognize that the stent 40 may be expanded using a variety of means and that the present invention is not limited strictly to balloon expansion.

Figure 3A:
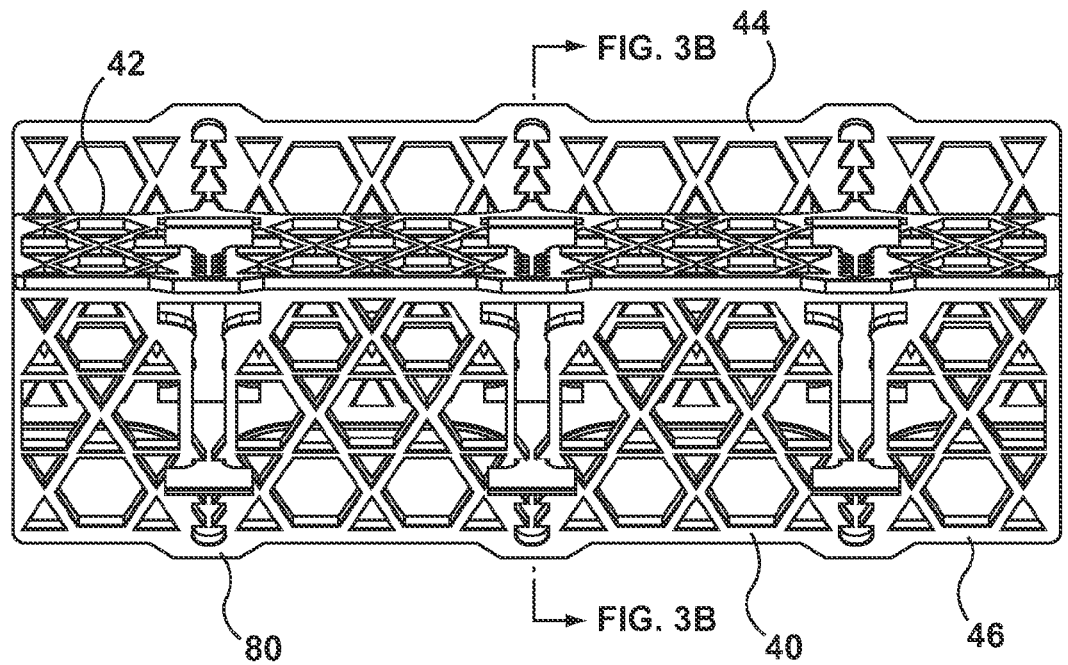
FIG. 3A is perspective view of a stent in an expanded configuration, in accordance with the present invention.
Figure 3B:
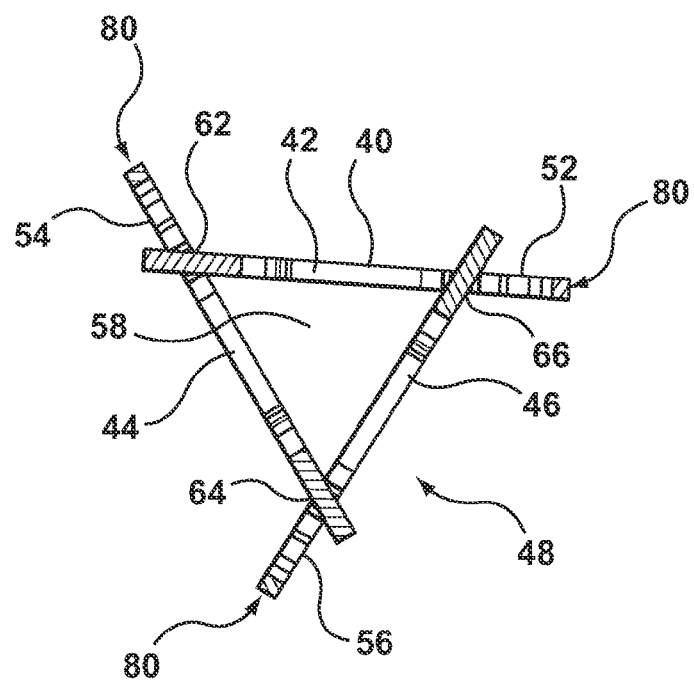
FIG. 3B is cross-sectional view of the stent shown in FIG. 3A.

Referring to FIGS. 3A and 3B, an assembled stent 40 in an expanded configuration is shown. In one embodiment, the stent 40 may be a generally tubular structure including a passageway that extends along a longitudinal axis. The overall length of the stent 40 is variable and depends on the site of application. Stent 40 is formed from at least one, and in this case three, stent units 42, 44, and 46 operably attached to one another (e.g., in a fan-shaped fashion). Referring to FIG. 3B, the stent units 42, 44, and 46, once assembled, form a single framework 48, with each unit including a flap portion 52, 54, and 56 that projects substantially beyond a central core region 58 of the stent 40. The orthogonal projection of flap portion 52, for example, to stent unit 44 defines the extended position of flap portion 52, although one skilled in the art will recognize that the angle and degree of projection may vary based on the stent design. In one embodiment, as shown, the central core region 58 is triangular in shape. Those skilled in the art will recognize that the shape of the core region may vary and may be, for example, round.

Figure 6:
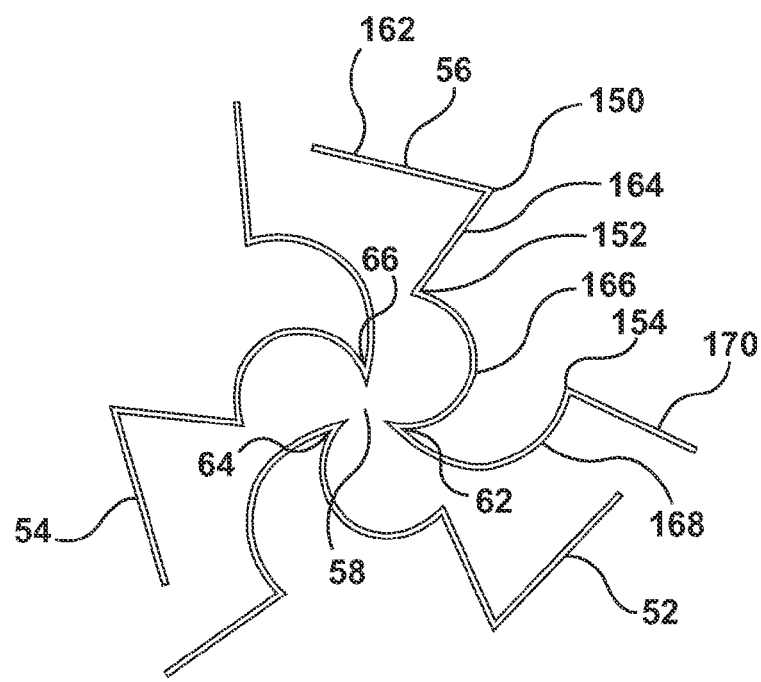
FIG. 6 is a cross-sectional view of an assembled stent in a partially compressed configuration, in accordance with the present invention.

In one embodiment, as illustrated in FIG. 6, at least one, and in this case three, pleats 62, 64 and 66 may be positioned at the intersection of the flap portions 52, 54, and 56 and the central core region 58. Pleats 62, 64 and 66 provide means for moving the flap portion 52, 54, and 56 (i.e., providing a degree of flexibility) between extended and compressed positions (described below). Pleats 62, 64 and 66 may consist of a more flexible material, a scoring in the material, hinges, and the like. In another embodiment, one or more other mechanism may provide means for moving the flap portion(s) between extended and compressed positions. In another embodiment, the flaps portions 52, 54, and 56 are movable between the extended and compressed positions without pleats. The pleats 62, 64, and 66, plus additional pleats, can be provided to divide the flap portions into flaplets between adjacent pleats which are radially stacked when the flap portion is in the compressed position. The stacking of the flaplets permits the stent to be compressed to a small diameter for delivery. In this example, the flap portion 56 includes pleats 150, 152, 154 in addition to pleat 62, which form flaplets 162, 164, 166, 168, 170. The flaps portions 52, 54 include pleats and flaplets like the flap portion 56, but are unnumbered for clarity of illustration.

Figure 4A:
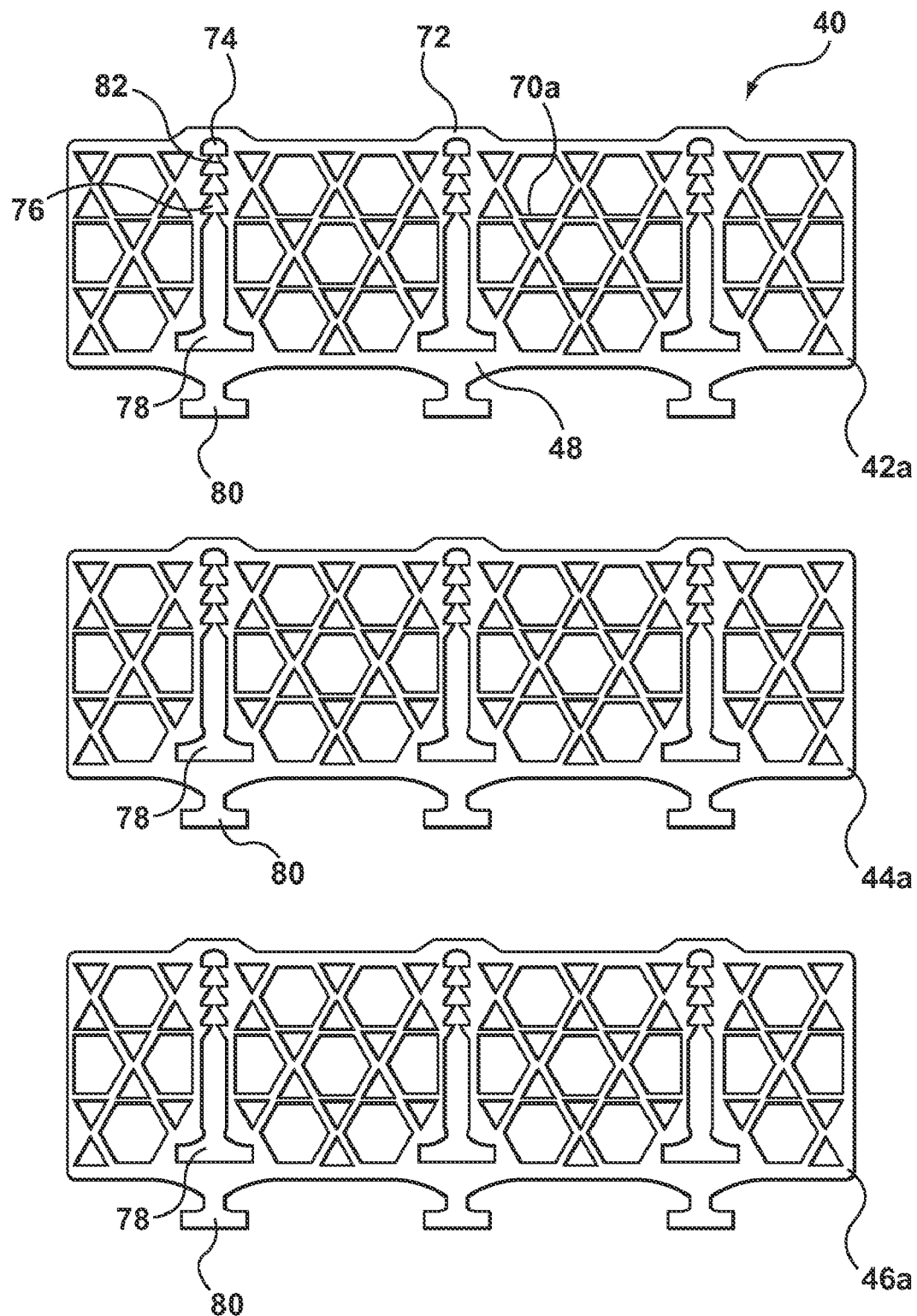
FIG. 4A is a perspective view of three stent units, in accordance with a first embodiment of the present invention.

Referring to FIG. 4A, in one embodiment, the three stent units 42a, 44a, 46a, include a plurality of struts 70a. Struts 70a are in a repeating triangle/hexagon pattern. In another embodiment, illustrated in FIG. 4B, the stent units 42b, 44b, 46b include similar struts 70b as the embodiment shown in FIG. 4A. In yet another embodiment, illustrated in FIG. 4C, the stent unit 42c, 44c, 46c struts 70c are in a hexagonal pattern. In yet another embodiment, the struts may be shaped and/or configured in a variety of different number, patterns, sizes, and configurations. In yet another embodiment, the stent unit(s) may include any combination of solid, porous, or other surface topographies. Those skilled in the art will recognize that the number, pattern, size, and configuration of the struts may vary from the illustrations and description provided herein.

Figure 4B:
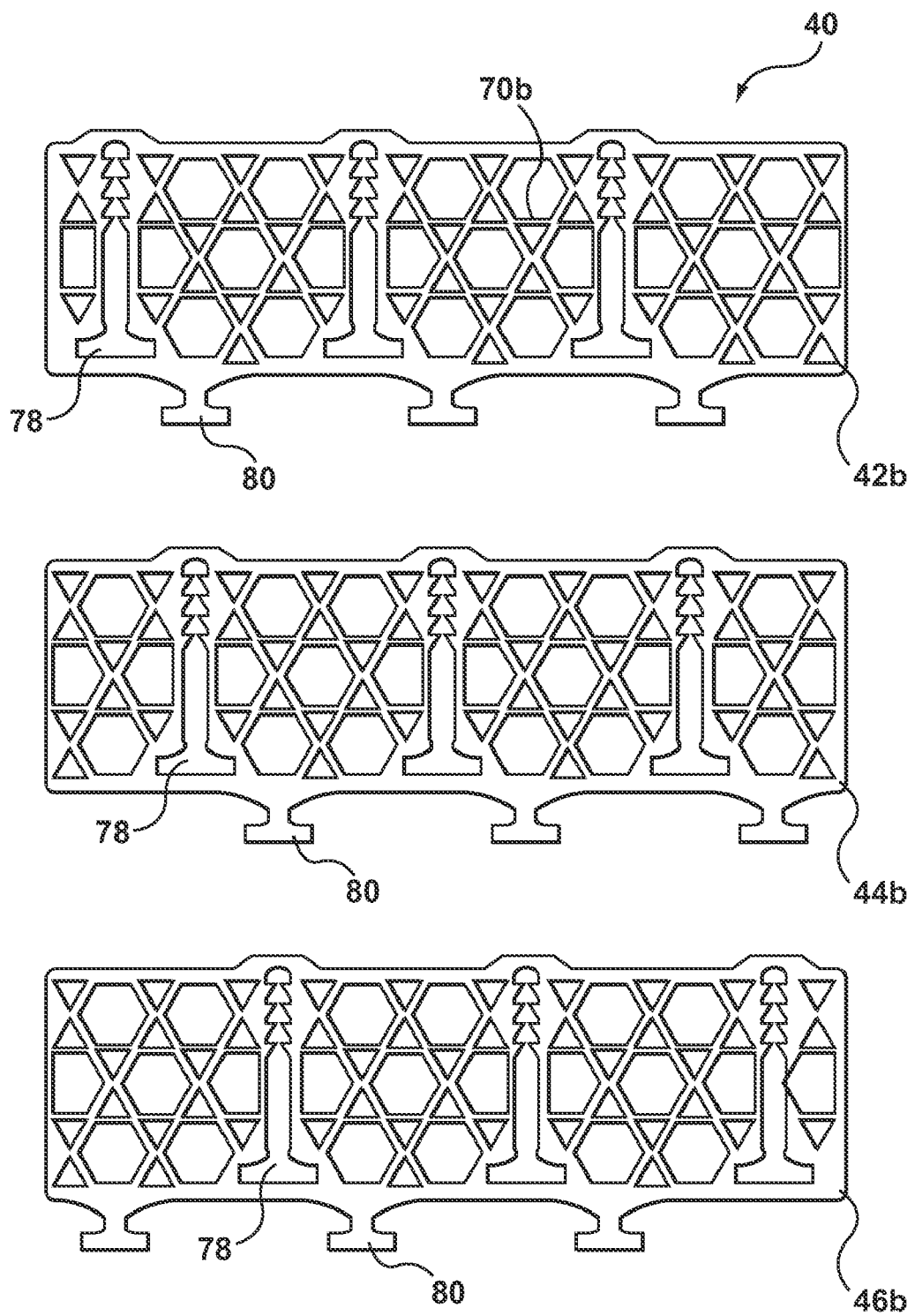
FIG. 4B is a perspective view of three stent units, in accordance with a second embodiment of the present invention.
Figure 4C:
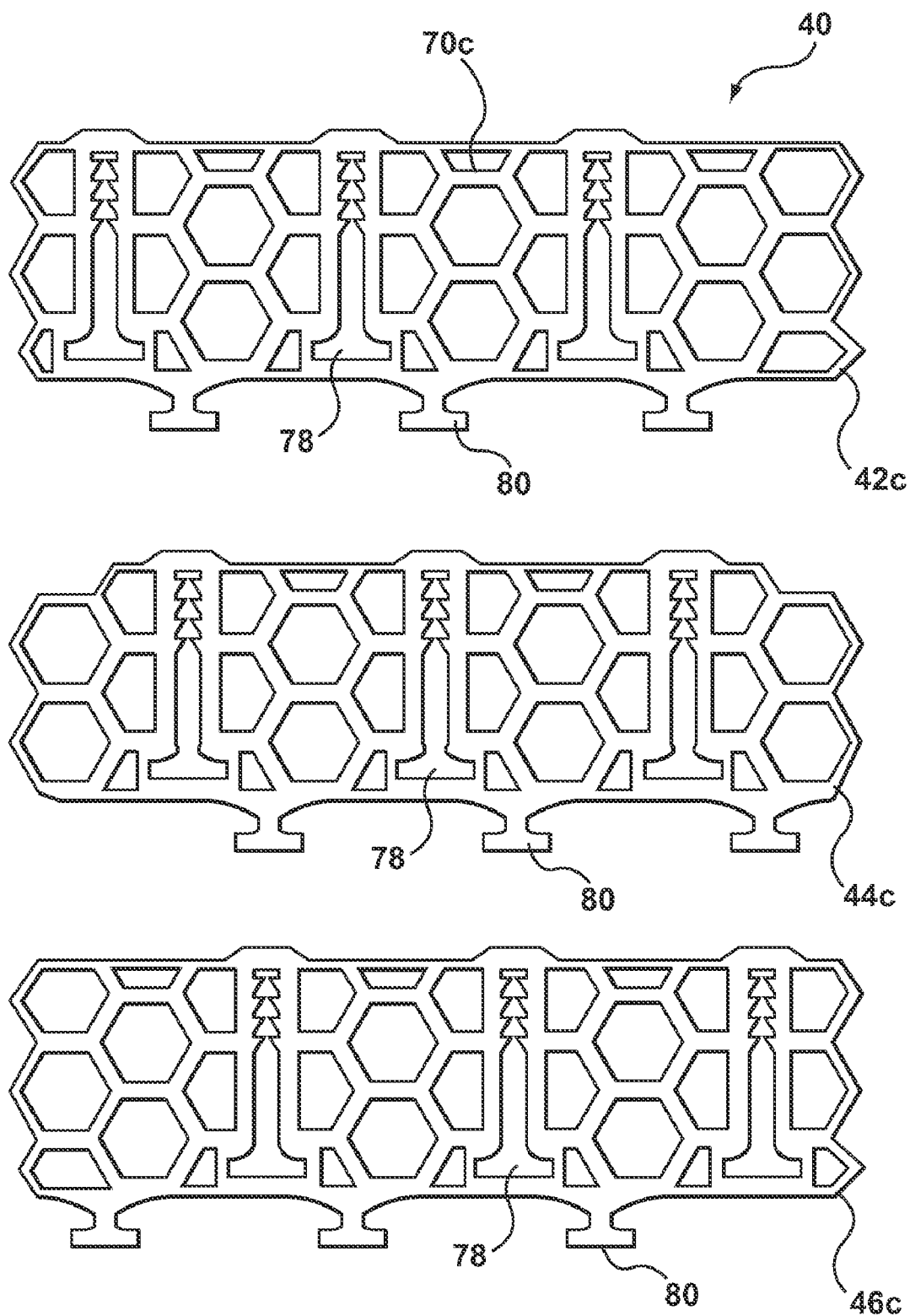
FIG. 4C is a perspective view of three stent units, in accordance with a third embodiment of the present invention.

Referring again to FIG. 4A, in one embodiment, a plurality of, and in this case three, lock assemblies 72 may be operably attached to each of the stent units 42a, 44a, and 46a. The lock assembly 72 may be a ratchet assembly 74, as illustrated in FIGS. 4A, 4B, and 4C, a hook, or other fastening means. The number of lock assemblies may vary, for example, based on such factors as the length of the stent, the stent material properties, and the external stresses exerted on the stent. The design of the stent 40 of the present invention may facilitate the lock assemblies to be assembled in a crimped or nearly crimped configuration thereby minimizing the magnitude of sliding movements (and resulting damage) as the stent 40 is loaded on the balloon 30 or other delivery device.

In one embodiment, the ratchet assembly 74 may include a lock portion 76 including an aperture 78 formed therein for receiving a tab portion 80 from an adjacent stent unit. Lock portion 76 may include a plurality of teeth 82 for progressively engaging the tab portion 80. Ratchet assemblies 74 allow sliding of the stent unit 42a in a direction of deployment (i.e., increasing inner diameter of the stent 40) while also minimizing recoil in a direction of compression (i.e., decreasing inner diameter of the stent 40).

Figure 7:
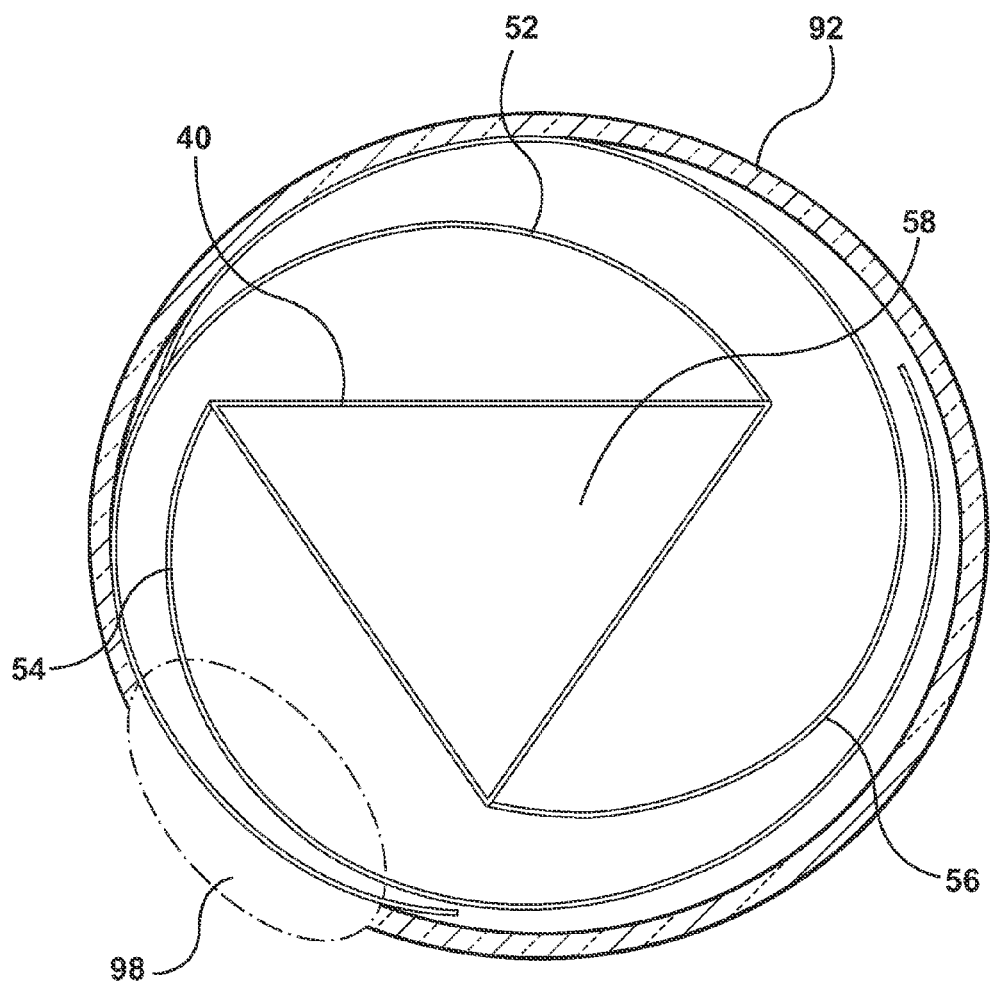
FIG. 7 is a cross-sectional view of a stent in a partially deployed configuration, in accordance with the present invention.

Tab portion 80 of stent unit 42a corresponds with an aperture 78 of adjacent stent unit 44a. Specifically, tab portion 80 of stent unit 42a is inserted into correspondingly shaped aperture 78 of stent unit 44a while the stent 40 is in the compressed configuration. As the stent 40 is deployed, the tab portion 80 of stent unit 42a slides toward the teeth 82 of stent unit 44a thereby ratcheting and locking the stent 40 into the deployed position, which is shown in FIG. 7.

In one embodiment, the tab portions 80 may be positioned substantially planar to the framework 48, thereby minimizing crossing profile. In one embodiment, planar tab portions are produced by laser cutting of polymeric sheets. In another embodiment, the tab portions may not be planar thereby potentially providing a greater locking force. In these embodiments, the non-planar tab portiosn may be produced by molding.

In one embodiment, as illustrated in FIG. 4A, the ratchet assembly 74 is positioned in a non-staggered configuration. Specifically, tab portions 80 of stent unit 42a, are aligned with (i.e., roughly parallel to) tab portions 80 of stent unit 44a. Likewise, tab portions 80 of stent unit 44a, are aligned with tab portions 80 of stent unit 46a. Finally, tab portions 80 of stent unit 46a, are aligned with tab portions 80 of stent unit 42a.

In another embodiment, as illustrated in FIGS. 4B and 4C, the ratchet assemblies 74 are positioned in a staggered configuration. Specifically, tab portions 80 of stent unit 42b, 42c are offset from (i.e., not parallel to) tab portions 80 of stent unit 44b, 44c, respectively. Likewise, the tab portions 80 of stent unit 44b, 44c are offset from (i.e., not parallel to) tab portions 80 of stent unit 46b, 46c, respectively. Finally, tab portions 80 of stent unit 46b, 46c are offset from tab portions 80 of the tab portions 80 of stent unit 42b, 42c, respectively.

The staggered configuration of the stent units 42b, 44b, 46b, 42c, 44c, and 46c allows for minimal overlap of the ratchet assemblies 74 one to another when the stent 40 is in the compressed configuration therefore providing a relatively small profile size. Those skilled in the art will recognize that the configuration of the lock assemblies may vary from the examples provided herein without departing from the spirit and scope of the present invention.

In one embodiment, the stent units 42, 44, and 46 may be manufactured from an inert, biocompatible material with high corrosion resistance. The biocompatible material may be plastically deformed at low-moderate stress levels. In another embodiment, the stent 40 may be of the self-expanding variety and the stent units 42, 44, and 46 manufactured from, for example, a nickel titanium alloy and/or other alloy(s) that exhibit superlastic behavior (i.e., capable of significant distortion without plastic deformation). Other suitable materials for the stent 40 include, but are not limited to, ceramic, cobalt, tantalum, stainless steel, titanium ASTM F63-83 Grade 1, niobium, high carat gold K 19-22, MP35N cobalt-based alloy, metals, metal alloys, and combinations thereof.

In one embodiment, the stent units 42, 44, and 46 may be manufactured by a thermal pressing, injection molding, or other process known in the art. In another embodiment, the stent units 42, 44, and 46 may be formed by laser cutting a biodegradable polymer film and assembled into a form, illustrated in FIGS. 3A and 3B. In one embodiment, the stent units 42, 44, and 46 may be assembled by inserting the ratcheted assemblies one to another. The stent 40 may them be loaded onto the balloon 30 and compressed (or "crimped") as known in the art for subsequent deployment.

Stent 40 may include at least one therapeutic agent 90 as part of one or more coatings. Application of the therapeutic agent 90 may be performed at numerous points during stent 40 manufacture (e.g. before laser cutting, after compression onto the balloon 30, etc.). The coatings may be positioned on various portions of the stent 40, especially on the flap portions 52, 54, and 56, which are conducive to receiving coatings placed thereon. This is an important advantage given the intimate contact between the flap portions 52, 54, and 56 and the vessel.

In one embodiment, the therapeutic agent 90 may comprise one or more drugs, polymers, a component thereof, a combination thereof, and the like. For example, the therapeutic agent may include a mixture of a drug and a polymer as known in the art. Some exemplary drug classes that may be included are antiangiogenesis agents, antiendothelin agents, antimitogenic factors, antioxidants, antiplatelet agents, antiproliferative agents, antisense oligonucleotides, antithrombogenic agents, calcium channel blockers, clot dissolving enzymes, growth factors, growth factor inhibitors, nitrates, nitric oxide releasing agents, vasodilators, virus-mediated gene transfer agents, agents having a desirable therapeutic application, and the like. Specific example of drugs include abciximab, angiopeptin, colchicine, eptifibatide, heparin, hirudin, lovastatin, methotrexate, streptokinase, taxol, ticlopidine, tissue plasminogen activator, sirolimus, trapidil, urokinase, zotarolimus, and growth factors VEGF, TGF-beta, IGF, PDGF, and FGF.

The polymer generally provides a matrix for incorporating the drug within the coating, or may provide means for slowing the elution of an underlying therapeutic agent when it comprises a cap coat. Some exemplary biodegradable polymers that may be adapted for use with the present invention include, but are not limited to, polycaprolactone, polylactide, polyglycolide, polyorthoesters, polyanhydrides, poly (amides), poly(alkyl-2-cyanocrylates), poly(dihydropyrans), poly(acetals), poly(phosphazenes), poly(dioxinones), trimethylene carbonate, polyhydroxybutyrate, polyhydroxyvalerate, their copolymers, blends, and copolymers blends, combinations thereof, and the like. Exemplary non-biodegradable polymers that may be adapted for use with the present invention may be divided into at least two classes. The first class includes hydrophobic polymers such as polyolefins, acrylate polymers, vinyl polymers, styrene polymers, polyurethanes, polyesters, epoxy, nature polymers, their copolymers, blends, and copolymer blends, combinations thereof, and the like. The second class includes hydrophilic polymers, or hydrogels, such as polyacrylic acid, polyvinyl alcohol, poly(N-vinylpyrrolidone), poly(hydroxy-alkylmethacrylate), polyethylene oxide, their copolymers, blends and copolymer blends, combinations of the above, and the like.

Solvents are typically used to dissolve the therapeutic agent and polymer to comprise a therapeutic agent coating solution. Some exemplary solvents that may be adapted for use with the present invention include, but are not limited to, acetone, ethyl acetate, tetrahydrofuran (THF), chloroform, N-methylpyrrolidone (NMP), methylene chloride, and the like.

Those skilled in the art will recognize that the nature of the drug and polymer may vary greatly and are typically formulated to achieve a given therapeutic effect, such as limiting restenosis, thrombus formation, hyperplasia, etc. Once formulated, a therapeutic agent solution (mixture) comprising the coating may be applied to the stent 40 by any of numerous strategies known in the art including, but not limited to, spraying, dipping, rolling, nozzle injection, and the like. Numerous strategies of applying the coating in accordance with the present invention are known in the art.

Figure 8:
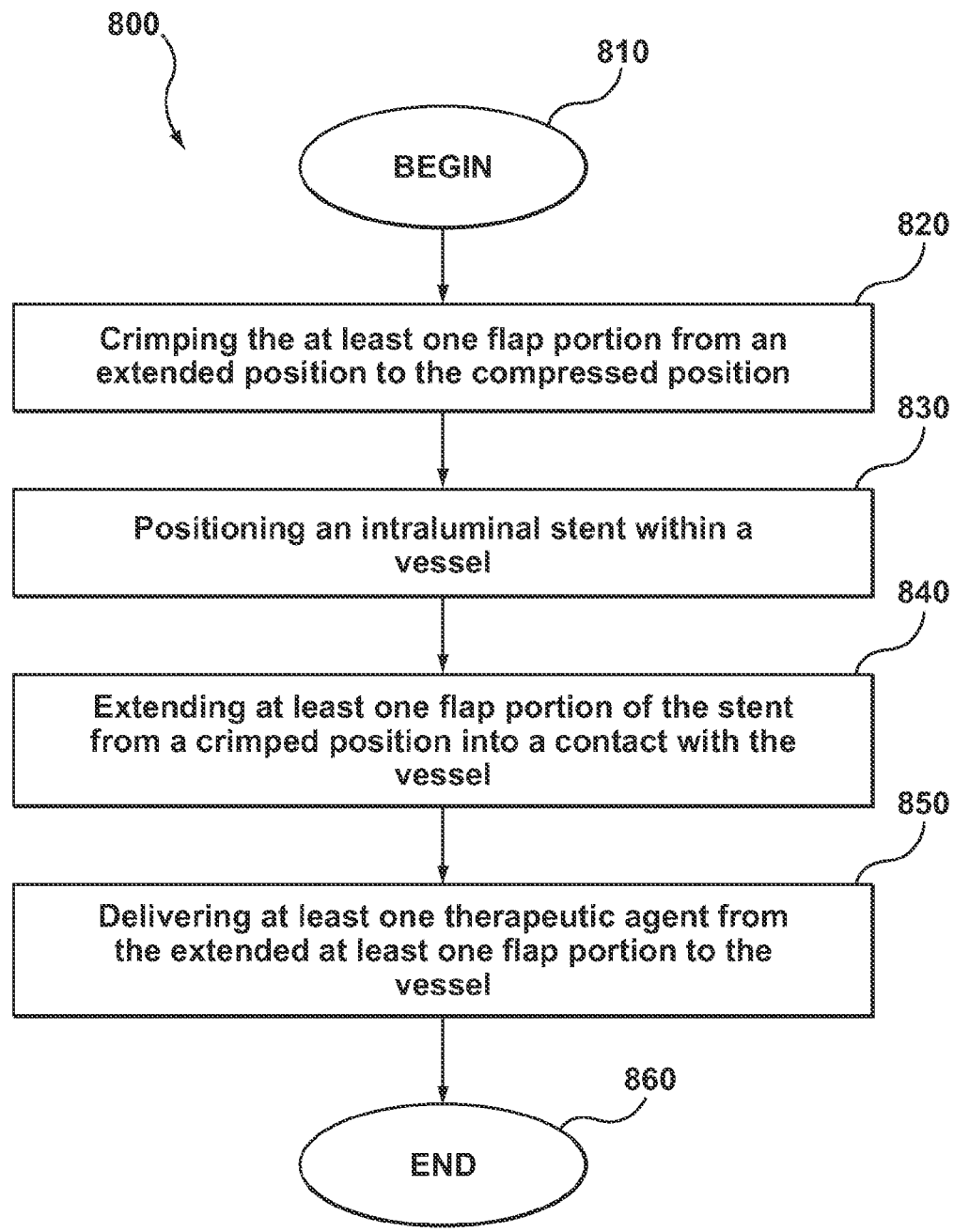
FIG. 8 illustrates a flowchart of a method of treating a vascular condition, in accordance with one embodiment of the present invention.

FIG. 8 illustrates a flowchart of a method 800 of treating a vascular condition, in accordance with one embodiment of the present invention. The treatment of a vascular condition, which in one embodiment may be an ischemic blood vessel narrowed by plaque deposits. The method may begin at step 810.

Figure 5:
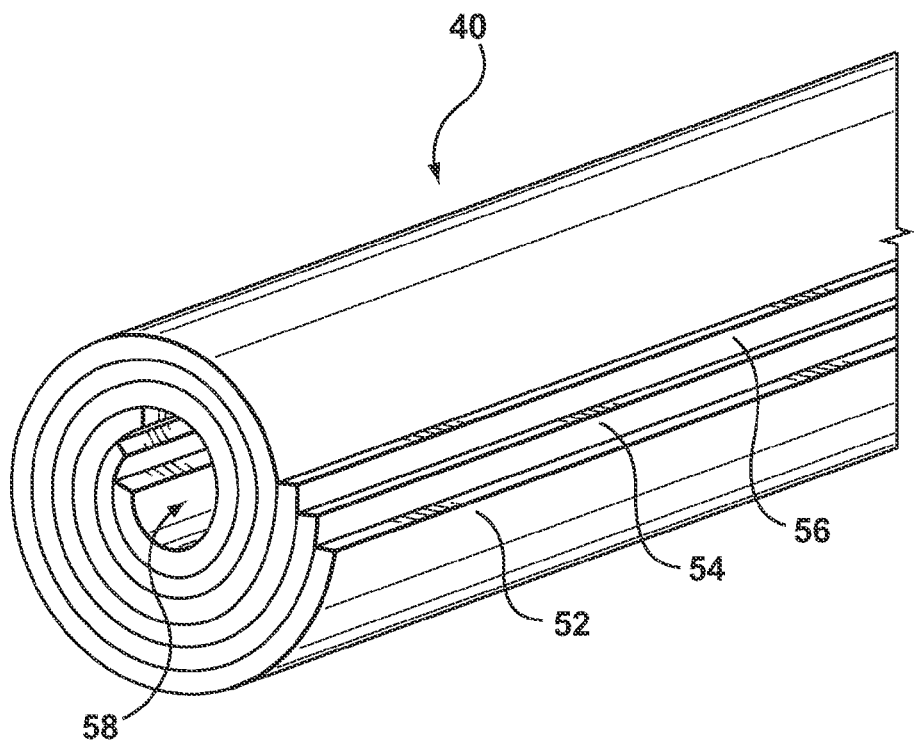
FIG. 5 is a cross-sectional view of an assembled stent in a compressed configuration, in accordance with the present invention.

At step 820, the flap portions 52, 54, and 56 of an assembled stent 40 may be crimped from the extended position, illustrated in FIGS. 3A and 3B, to an intermediate position, illustrated in FIG. 6, and finally to a compressed position, illustrated in FIG. 5, for subsequent deployment. Numerous methods may be adapted by those skilled in the art to achieve crimping to, for example, reduce injury to the stent 40 and to retain a small profile size. In one embodiment, the crimping may occur along the pleats 62, 64 and 66, as shown in FIG. 6. Once compressed (crimped), the stent resembles a tightly wound spiral (e.g., a "fresh rose").

At step 830, the stent 40 is positioned within a vessel. In one embodiment, at least one (radiopaque) marker may be disposed on the stent 40, catheter 20, and or component thereof to allow in situ visualization and proper advancement, positioning, and deployment of the stent 40. The marker(s) may be manufactured from a number of materials used for visualization in the art including radiopaque materials platinum, gold, tungsten, metal, metal alloy, and the like. Marker(s) may be visualized by fluoroscopy, IVUS, and other methods known in the art. Those skilled in the art will recognize that numerous devices and methodologies may be utilized for positioning an intraluminal stent in accordance with the present invention.

Once the stent 40 is properly positioned, the flap portions 52, 54, and 56 are extended (step 840) from the compressed position, illustrated in FIG. 5. Stent 40 may move radially outward from the longitudinal axis as the stent 40 is deployed, while recoil is minimized (described above). Specifically, the central core region 58 may expand in profile size while the flap portions 52, 54, and 56 extend from the compressed position along to the extended position until contact is made with a vessel wall 92, as shown in FIG. 7. The flap portions 52, 54, and 56 gradually expand until contact with the vessel wall 92 is made. In other words, the tightly wound spiral (e.g., the "fresh rose") unfurls after deployment. At final deployment, the central core region 58 will fully expand to fill the vessel interior, with the flap portions flattened against the vessel walls.

At this point, the stent 40 may be fully secured against the vessel wall 92. Additional measures, such as anchors or adhesives, may be used to further secure the stent 40 to the vessel wall 92. The degree that any of the flap portions 52, 54, and 56 has for extension, allows the stent 40 to conform to the shape of round, semi-round, and "irregularly" shaped vessels, including those with lesions 98.

In one embodiment, the stent 40 may be expanded with the balloon 30. As the flap portions 52, 54, and 56 are extended, they may extend along the pleats 62, 64 and 66, as shown in FIG. 6. In one embodiment, the flap portions may be manufactured from resilient material to assist extension after stent 40 deployment. Before deployment, one or more mechanisms may ensure the flaps portions 52, 54, and 56 are maintained in the compressed position (e.g., a heat sensitive adhesive, a lock, and the like). In another embodiment, other means may be used for promoting extension and maintaining compression of the flap portions.

Balloon 30 may then be deflated and retracted thereby allowing the stent 40 to remain in a deployed configuration. In another embodiment, the stent may be of a self-expanding variety as known in the art. The advancement, positioning, and deployment of stents and like devices are well known in the art. In addition, those skilled in the art will recognize that numerous devices and methodologies may be adapted for deploying the stent in accordance with the present invention.

At step 850, at least one therapeutic agent is delivered from a portion of the extended at least one flap portion to the vessel wall 92. Regardless of the shape of the vessel, the stent 40 may be better capable of conforming to it, such as when plaque buildup 94 is present. As such, the therapeutic agent may be delivered more effectively.

The method may be terminated at step 860.

While the embodiments of the invention disclosed herein are presently considered to be preferred, various changes and modifications can be made without departing from the spirit and scope of the invention. For example, the number of stent units (e.g., single or multiple unit designs), lock assemblies, struts, and flap portions are not limited to the illustrated and described embodiments.

Upon reading the specification and reviewing the drawings hereof, it will become immediately obvious to those skilled in the art that myriad other embodiments of the present invention are possible, and that such embodiments are contemplated and fall within the scope of the presently claimed invention. The scope of the invention is indicated in the appended claims, and all changes that come within the meaning and range of equivalents are intended to be embraced therein.

The invention claimed is:

1. An intraluminal stent comprising a framework, the framework including a plurality of stent units, each stent unit having a flexible flap portion projecting substantially beyond a central core region and movable from a compressed position to an extended position when the stent is deployed, the flexible flap portions including an edge portion and side portion, the side portion configured to make contact with and conform to a vessel wall when the stent is deployed, wherein the plurality of flap portions comprise at least one pleat, the pleat dividing at least one of the plurality of flap portions into flaplets, the flaplets being stacked radially when the flap portion is in the compressed position; and a plurality of lock assemblies attached to the stent unit, wherein the plurality of lock assemblies comprise ratchet assemblies for allowing sliding of the stent unit in a direction of deployment and minimizing recoil in a direction of compression.

2. The stent of claim 1 wherein the stent comprises at least one biodegradable component.

3. The stent of claim 1 wherein the plurality of lock assemblies comprise at least one of a staggered configuration and a non-staggered configuration.

4. The stent of claim 1 further comprising at least one therapeutic agent disposed on at least one of the plurality of flap portions.

5. The stent of claim 1 wherein in the deployed extended position, the central core region is expanded to fill the vessel and the flexible flap portions are flattened against the vessel wall.

6. An intraluminal stent delivery system comprising:
a catheter; and
an intraluminal stent comprising:
a framework, the framework including a plurality of stent units, each stent unit having a flexible flap portion projecting substantially beyond a central core region and movable from a compressed position to an extended position when the stent is deployed, the flexible flap portions including an edge portion and side portion, the side portion configured to make contact with and conform to a vessel wall when the stent is deployed, wherein the plurality of flap portions comprise at least one pleat, the pleat dividing at least one of the plurality of flap portions into flaplets, the flaplets being stacked radially when the flap portion is in the compressed position; and a plurality of lock assemblies operably attached to the stent unit, wherein the plurality of lock assemblies comprise ratchet assemblies for allowing sliding of the stent unit in a direction of deployment and minimizing recoil in a direction of compression.

7. The system of claim 6 wherein the stent comprises at least one biodegradable component.

8. The system of claim 6 wherein the plurality of lock assemblies comprise at least one of a staggered configuration and a non-staggered configuration.

9. The system of claim 6 further comprising at least one therapeutic agent disposed on at least one of the plurality of flap portions.

10. A method of treating a vascular condition, the method comprising:
positioning an intraluminal stent within a vessel the stent comprising a framework, the framework including a plurality of stent units, each stent unit having a flexible flap portion projecting substantially beyond a central core region, each flap portion comprising at least one pleat, the pleat dividing at least one of the plurality of flap portions into flaplets, the flaplets being stacked radially when the flap portion is in a compressed position; and a plurality of lock assemblies operably attached to the stent unit, wherein the plurality of lock assemblies comprise ratchet assemblies for allowing sliding of the stent unit in a direction of deployment and minimizing recoil in a direction of compression;
extending the plurality of flap portions of the stent from the compressed position;
unfolding the at least one pleat of each of the flap portions;
contacting a side portion of the flap portions against a wall of the vessel; and
conforming the side portions of the flap portions to a shape of the vessel wall.

11. The method of claim 10 wherein positioning the stent comprises sliding of the stent in a direction of deployment and minimizing recoil in a direction of compressing.

12. The method of claim 10 further comprising delivering at least one therapeutic agent from at least one flap portion to the vessel.

\* \* \* \* \*